US008876838B2

(12) United States Patent
Winiarski

(10) Patent No.: US 8,876,838 B2
(45) Date of Patent: Nov. 4, 2014

(54) ANTI-CHOKING DEVICE

(76) Inventor: Kevin Winiarski, Swartz Creek, MI (US)

( * ) Notice: Subject to any disclaimer, the term of this patent is extended or adjusted under 35 U.S.C. 154(b) by 1068 days.

(21) Appl. No.: 12/372,759

(22) Filed: Feb. 18, 2009

(65) Prior Publication Data

US 2009/0228018 A1    Sep. 10, 2009

Related U.S. Application Data

(60) Provisional application No. 61/034,544, filed on Mar. 7, 2008.

(51) Int. Cl.
- *A61D 1/12* (2006.01)
- *A61M 16/06* (2006.01)
- *A61M 16/00* (2006.01)

(52) U.S. Cl.
CPC ....... *A61M 16/06* (2013.01); *A61M 2205/8225* (2013.01); *A61M 16/0009* (2014.02)
USPC ............. 606/106; 604/317; 604/319

(58) Field of Classification Search
USPC .......... 606/106; 604/77, 73, 76, 79, 317–324; 128/200.14–200.23, 205.19; 15/300.1
See application file for complete search history.

(56) References Cited

U.S. PATENT DOCUMENTS

| | | | |
|---|---|---|---|
| 2,292,474 A | 8/1942 | Paxton | |
| 3,502,069 A | 3/1970 | Silverman | |
| 3,716,307 A * | 2/1973 | Hansen | 417/191 |
| 3,946,736 A | 3/1976 | Neward | |
| 4,287,819 A | 9/1981 | Emert | |
| 4,400,168 A | 8/1983 | Buechel et al. | |
| 4,535,765 A | 8/1985 | Paoluccio et al. | |
| 4,662,367 A | 5/1987 | Gore, Jr. | |
| 4,764,167 A | 8/1988 | Tu | |
| 4,787,894 A | 11/1988 | Turnbull | |
| 4,790,818 A * | 12/1988 | DeLuca et al. | 604/540 |
| 4,791,914 A | 12/1988 | May | |
| 4,813,931 A | 3/1989 | Hauze | |
| 4,947,841 A | 8/1990 | Ng | |
| 4,971,053 A | 11/1990 | Tarrats | |
| 5,071,412 A | 12/1991 | Noda | |
| 5,167,621 A | 12/1992 | Band et al. | |
| 5,609,149 A | 3/1997 | Takach | |
| 5,665,080 A | 9/1997 | Vandenberg | |
| 5,782,837 A * | 7/1998 | York | 606/106 |
| 5,921,970 A | 7/1999 | Vandenberg | |
| 6,135,980 A | 10/2000 | Vu | |
| 6,478,770 B1 * | 11/2002 | Litkouhi et al. | 604/77 |
| 6,500,164 B1 | 12/2002 | Turner et al. | |
| 6,631,713 B1 | 10/2003 | Christopher | |
| 6,986,773 B1 | 1/2006 | Manougian | |
| 7,351,245 B2 * | 4/2008 | Rozinsky et al. | 606/106 |
| 2010/0241026 A1 * | 9/2010 | Boukas | 600/562 |

* cited by examiner

*Primary Examiner* — Darwin Erezo
*Assistant Examiner* — Katrina Stransky
(74) *Attorney, Agent, or Firm* — Brooks Kushman P.C.

(57) ABSTRACT

An apparatus for use in dislodging a particle from a choking person's airway. The apparatus including a venturi vacuum pump, a source of compressed fluid and a mask. The apparatus operating such that after the mask is placed over the choking person's nose and mouth, compressed fluid flowing through the venturi vacuum pump generates a low pressure region in the mask and correspondingly the person's airway which dislodges the particle.

19 Claims, 3 Drawing Sheets

ANTI-CHOKING DEVICE

CROSS-REFERENCE TO RELATED APPLICATIONS

This application claims the benefit of U.S. Provisional Application Ser. No. 61/034,544 filed on Mar. 7, 2008.

FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention is directed toward an apparatus for dislodging an object located in a person's airway, and more specifically to an apparatus using a source of compressed fluid to create a negative pressure region to dislodge the object.

2. Description of Related Art

Choking because of an obstructed airway is a leading cause of accidental death. If a choking person is unable to cough or speak then the person needs immediate aid. One type of aid is for a second person to perform what is termed the Heimlich maneuver by placing the second person's arms around the choking person and delivering a squeeze/thrust motion to the choking person's abdomen to make the diaphragm move air out of the choking person's lungs, creating a kind of artificial cough. The cough intended to move and expel an obstructing foreign body lodged in the airway. Each thrust should be given with the intent of removing the obstruction. In an instance where a second person is unavailable or does not understand how to perform the Heimlich maneuver, it is possible for an individual to attempt to perform the Heimlich maneuver or abdominal thrusts on themselves using a fixed object such as a railing or chair. Even when done correctly, the Heimlich maneuver can result in injury to the choking person.

In addition, apparatuses that operate to generate a low pressure or a vacuum in the person's mouth or throat above the obstruction and thereby create some type of suction to dislodge an object lodged in a person's airway are known in the prior art. Typically, these devices use some type of diaphragm or piston to create the vacuum or low-pressure region. For example, U.S. Pat. No. 4,287,819 to Emerit discloses a source of vacuum in which a piston combined with a piston rod is axially slidable in a tubular body. A suction orifice is located along the axis of the body. This portable source of vacuum makes it possible to exert a suction on oneself at practically any point on the body for the purpose of drawing off the venom of a sting or bite after having applied the suction orifice in a sealed manner on the skin of a person.

A fluid extractor described in U.S. Pat. No. 5,167,621, issued to David M. Band et al. on Dec. 1, 1992, generates vacuum by subjecting a diaphragm to an external source of vacuum. While the device of Band et al. includes a mouthpiece, this is different from the facemask of the present invention, which seals pneumatic pressure at the face of a user subjected to vacuum for extracting a foreign object from the breathing passageways.

Takach, U.S. Pat. No. 5,609,149, discloses an anti-choking device of the type wherein a suction device utilizing a manual pump to develop a partial vacuum on its down-stroke, and includes tubes and attachments for holding the device against the victim's mouth. Excessive vacuum, which could be harmful to the victim, is limited by construction of the plunger inducing a vacuum. The plunger deflects or yields if excess vacuum is developed, thereby allowing air to bypass the plunger and relieve the vacuum.

SUMMARY OF THE INVENTION

According to a preferred embodiment of the present invention, there is provided an apparatus for assisting a choking person with removal of an object lodged in the person's airway. The apparatus includes a venturi vacuum generator having an inlet port, an exhaust port and a vacuum port. A source of compressed fluid coupled to the inlet port flows through a nozzle of the venturi vacuum generator thereby drawing entrained air through the vacuum port. A mask is attached to the vacuum port, typically through a tube or conduit, wherein the mask is placed over the user's nose and mouth. Actuation of the venturi vacuum generator creates a negative pressure region in the person's mouth, which operates to dislodge the food particle or other object from the person's airway.

According to at least one embodiment of the present invention, a device for dislodging an object obstructing a person's airway includes a through passage having an inlet port at one end and an exhaust port at an opposite end, such that the inlet port defines a bore having a first cross section. The device further includes a vacuum passage connected to the through passage between the inlet port and the exhaust port of the through passage, the vacuum passage including a vacuum outlet port and a vacuum inlet port communicating with the through passage. The device may also include a nozzle disposed within the through passage, the nozzle including a constricted portion defining a bore having a second cross section of lesser area than the first cross section. Additionally, the device includes a source of pressurized air having a release port mounted to the inlet port of the through passage, whereby airflow from the source of pressurized air through the through passage creates a suction force at the outlet port of the vacuum passage capable of dislodging the object obstructing the person's airway. The constricted portion of the nozzle may by characterized by a frustoconical shape.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
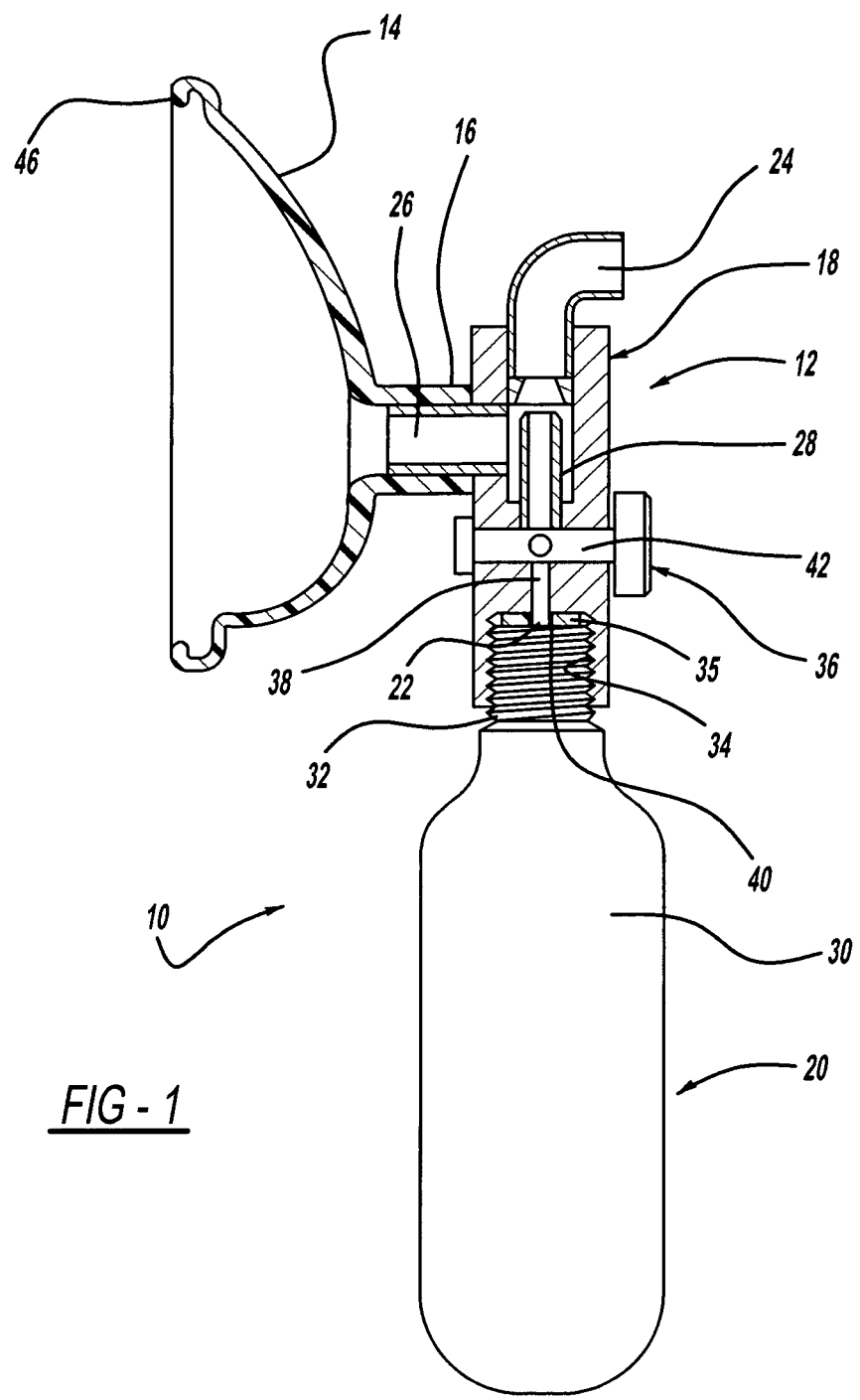
FIG. 1 is a side view, with portions removed for clarity, of one embodiment of the present invention.

FIG. 1 illustrates one embodiment of an apparatus for dislodging an object located in a person's airway, seen generally at 10, wherein the apparatus 10 includes a vacuum generator, seen generally at 12, attached to a mask 14 via a tube or conduit 16. The vacuum generator 12 includes a venturi vacuum pump 18 and a source or supply of compressed fluid 20 stored in some type of container. The venturi vacuum pump 18 includes an inlet port 22, an exhaust port 24 and a vacuum port 26. The venturi vacuum pump 18 includes a nozzle 28 positioned between the inlet port 22 and the exhaust port 24. As the compressed fluid 20 flows through the nozzle 28, it causes a venturi action. Specifically, as the compressed fluid 20 flows through the nozzle 28 the velocity thereof increases and its pressure decreases. Accordingly, as the compressed fluid 20 expands and flows through the nozzle 28 it creates a pressure lower than atmospheric pressure that pulls or draws surrounding air or fluid in through the vacuum port 26 creating a negative pressure or vacuum flow. The entrained air as well as the compressed fluid 20 exhausts through the exhaust port 24 into the atmosphere.

In one embodiment, carbon dioxide or $CO_2$ is a source of compressed fluid 20 used with the venturi vacuum pump 18. Other sources of compressed fluid 20 such as compressed nitrogen or compressed nitrous oxide can also be used and in some instances, such as those where the apparatus 10 will be used under varying temperature conditions may be preferable. As illustrated in FIG. 1, a compressed fluid cartridge or cylinder 30 is attached or secured to the venturi vacuum pump 18. The cartridge 30 can be attached in several ways, typically with a plurality of threads 32 on the cartridge 30 engaging a complementary plurality of threads 34 on the venturi vacuum pump 18. Accordingly, the cartridge 30 screws onto the venturi vacuum pump 18 with the upper surface of the cartridge 30 engaging a seal member 35.

The apparatus 10 also includes a release mechanism, seen generally at 36, used to release the compressed fluid 20 from the cartridge 30. One example of a release mechanism 36 includes a piercing pin 38 that pierces a seal 40 located at the upper surface of the cartridge 30, which enables the compressed fluid 20 to escape the cartridge 30 and flow through the venturi vacuum pump 18. The release mechanism 36 may also include a metering valve 42 to control the flow of the compressed fluid 20 from the cartridge 30. Thus, opening the metering valve 42 to different positions controls the flow rate of compressed fluid 20.

It should be understood that the various release mechanisms for attaching a cartridge containing a compressed fluid to a device using the compressed fluid are known. Some release mechanisms release the compressed fluid in a single step; i.e., once the seal is pierced the entire contents of the cartridge are evacuated. Other release mechanisms that measure or meter and thus control the amount of compressed fluid released from the cartridge are also suitable. The present invention contemplates the use of these various release mechanisms 36 depending upon the results desired, with the release mechanism 36 disclosed herein being but one example of a mechanism for releasing the compressed fluid 20 from the cartridge 30. For example in some instances it may be desirable to use a simple release mechanism 36 wherein the cartridge 30 is located in a housing and spaced from the piercing pin 38. To activate the apparatus 10, the cartridge 30 forced against the piercing pin 38, which pierces the seal 40 thus allowing the compressed fluid 20 to flow through the venturi vacuum pump 18. Another example involves attaching the cartridge 30 to the venturi vacuum pump 18 such that the seal 40 on the cartridge 30 is pierced and using a gate-type valve attached to a release pin wherein pulling the release pin opens the gate valve allowing the compressed fluid 20 to flow freely through the venturi vacuum pump 18. As will be understood by one of ordinary skill in the art the object of the release mechanism 36 is to release a compressed fluid 20 from the cartridge 30 whereby it flows through the venturi vacuum pump 18 generating a vacuum or negative pressure area at the vacuum port 26.

Figure 3:
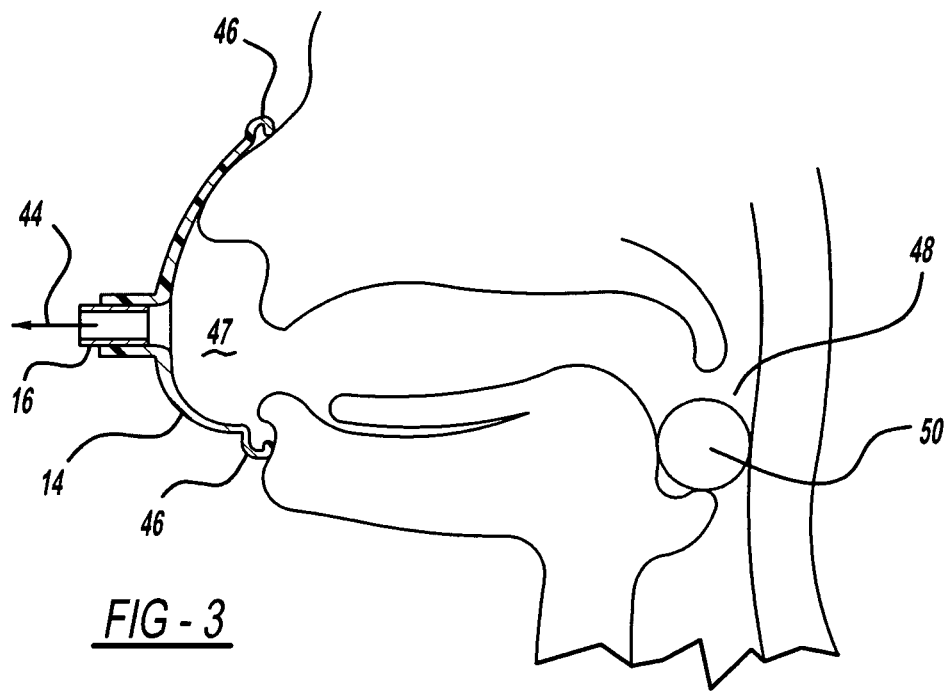
FIG. 3 is a schematic view showing a portion of the apparatus according to the first embodiment in a use position.

As set forth above, a mask 14 is attached to the vacuum port 26 via a tube or conduit 16. In use, as illustrated in FIG. 3, the mask 14 is placed over the user's nose and mouth with the seal lip 46 of the mask 14 engaging the person's face to create a chamber 47. Actuation of the release mechanism 36 releases the compressed fluid 20 from the cartridge 30 whereby the compressed fluid 20 flows through the venturi vacuum pump 18 and generates a negative pressure area in the chamber 47 by drawing air from the chamber 47 and the person's mouth in the direction of the arrow 44. Correspondingly this creates a pressure differential between the respective sides of a food particle or morsel 50 lodged in the person's airway or throat 48. The pressure differential dislodges the food particle 50 and thereby removes the obstruction.

Figure 2:
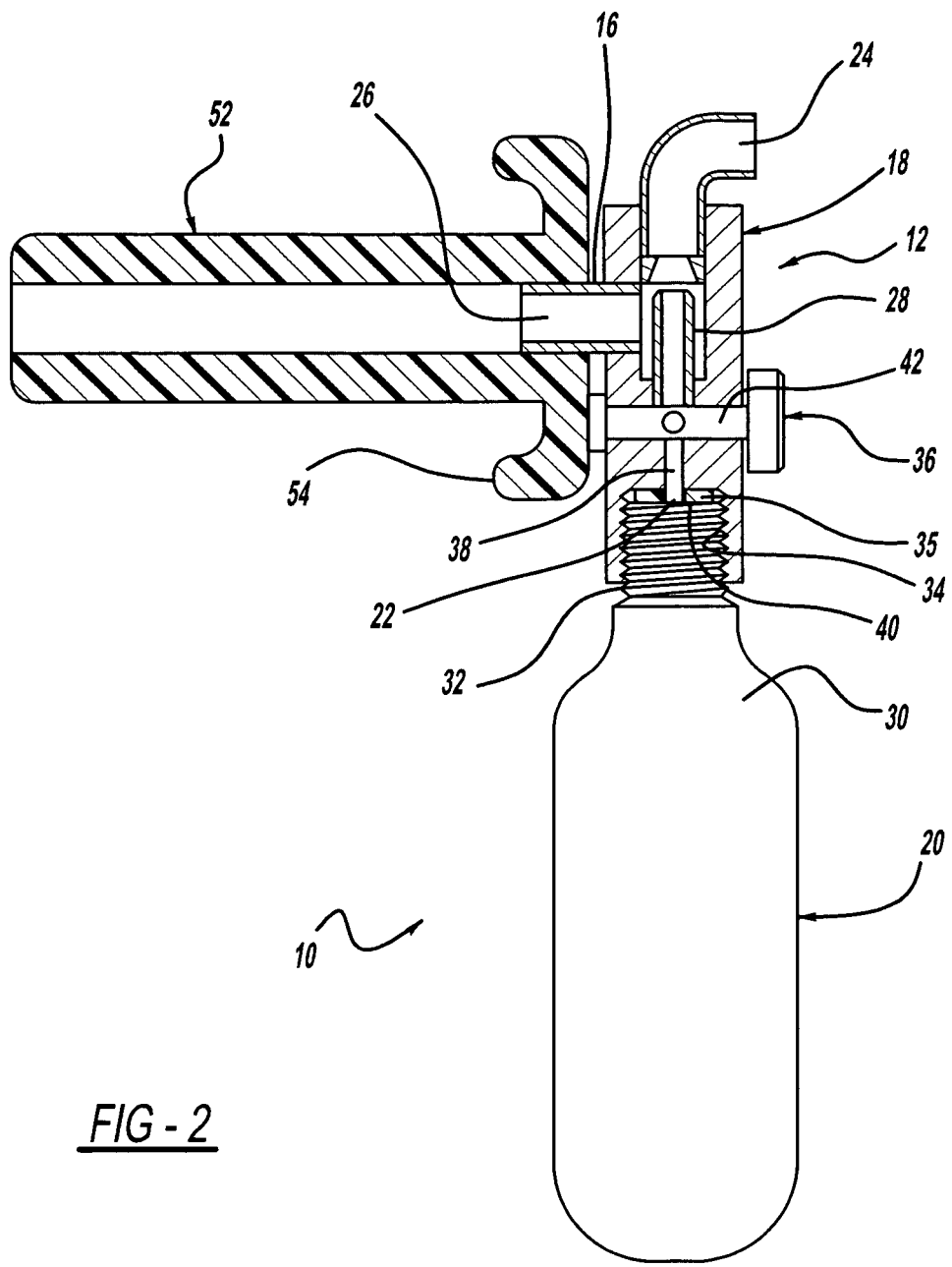
FIG. 2 is a side view, with portions removed for clarity, of a second or alternative embodiment of the present invention.
Figure 4:
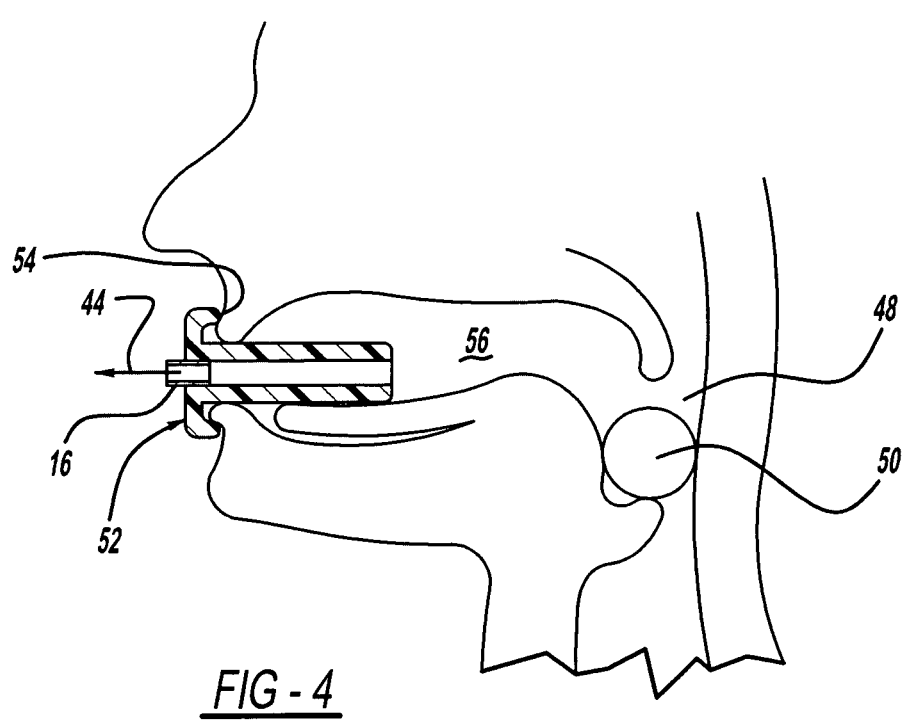
FIG. 4 is a schematic view showing a portion of the apparatus according to the second embodiment in a use position.

FIG. 2 illustrates another embodiment of the apparatus 10 utilizing a venturi vacuum pump 18 connected to a mouth tube 52 instead of a mask 14. As illustrated in FIG. 4, the mouth tube 52 is inserted into the choking person's mouth and extends into the throat past the tongue to depress the tongue and prevent possible blockage of the airway by the tongue. The mouth tube 52 includes a seal member 54 that engages the person's lips to create a seal around the mouth. As with the previous embodiment, the actuation of the release mechanism 36 enables compressed fluid 20 to flow through the venturi vacuum pump 18, which creates a negative pressure area 56 or vacuum to dislodge the food particle or morsel 50 located in the person's airway 48. When using the mouth tube 52 it may be necessary to pinch the person's nose to create a seal and prevent air from being drawn in through the nasal cavity.

It should be understood that the present apparatus 10 is suitable for dislodging particles other than food particles or morsels 50 that are set forth herein for the purpose of example. In addition, the mask 14 and mouth tube 52 can be formed of a high strength yet disposable material such as plastic wherein after a single use the mask 14 or mouth tube 52 can be removed from the venturi vacuum pump 18 and discarded.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A device for dislodging an object obstructing a person's airway comprising:
 a through passage having a through portion including an inlet port at one end and an exhaust port at an opposite end;
 a curved passage forming a portion of the exhaust port and extending away from the through portion;
 a vacuum passage connected to the through passage at a connection region between the inlet port and the exhaust port of the through passage, the vacuum passage including a vacuum outlet port and a vacuum inlet port communicating with the through passage; and a source of pressurized air having a release port mounted to the inlet port of the through passage, whereby airflow from the source of pressurized air creates a first directional airflow through the through passage at the connection region and a second directional airflow through the vacuum passage in a direction substantially normal to the first directional airflow such that the second directional airflow creates a vacuum capable of dislodging the object obstructing the person's airway.

2. The device of claim 1 further comprising a nozzle disposed within the through passage, the nozzle including a constricted portion defining a bore having a cross section of lesser area than the cross section of the through passage near the inlet port.

3. The device of claim 1, wherein a first longitudinal axis extending between the inlet port and the connection region of the through passage is substantially aligned with a second longitudinal axis extending between the release port of the source of pressurized air and a base portion of the source of pressurized air opposite the release port.

4. The device of claim 1 further comprising a mask connected to and in communication with the vacuum passage.

5. The device of claim 1 further comprising a mouth tube connected to and in communication with the vacuum passage.

6. The device of claim 1 further comprising a piercing pin disposed within the through passage for piercing a seal covering the release port of the source of pressurized air.

7. A device for dislodging an object obstructing a person's airway comprising:
a through passage having an inlet port at one end and an exhaust port at an opposite end;
a vacuum passage connected to the through passage at a connection region between the inlet port and the exhaust port of the through passage, the vacuum passage including a vacuum outlet port and a vacuum inlet port communicating with the through passage;
a mouth tube connected to and in communication with the vacuum outlet port for engaging a person's airway; and
a compressed fluid container having at one end a release port mounted to the inlet port of the through passage and a base portion at an opposite end, wherein a primary axis extending between the release port and the base portion of the compressed fluid container is substantially aligned with a secondary axis extending between the inlet port and the connection region of the through passage; and
wherein airflow from the source of pressurized air creates a first directional airflow through the through passage, at the connection region and a second directional airflow through the vacuum passage in a direction substantially normal to the first directional airflow such that the second directional airflow creates a vacuum capable of dislodging the object obstructing the person's airway.

8. The device of claim 7 further comprising a nozzle disposed within the through passage, the nozzle including a constricted portion defining a bore having a cross section of lesser area than the cross section of the through passage near the inlet port.

9. The device of claim 7 further comprising a mouth tube connected to and in communication with the vacuum passage.

10. The device of claim 7 further comprising a piercing pin disposed within the through passage for piercing a seal covering the release port of the source of pressurized air.

11. A device for dislodging an object obstructing a person's airway comprising:
a through passage having a through portion including an inlet port at one end and an exhaust port at an opposite end, the inlet port defining a first bore having a first cross section;
a curved passage forming a portion of the exhaust port and extending away from the through portion;
a vacuum passage connected to the through passage between the inlet port and the exhaust port of the through passage, the vacuum passage including a vacuum outlet port and a vacuum inlet port communicating with the through passage;
a nozzle disposed within the through passage, the nozzle including a constricted portion defining a second bore having a second cross section of lesser area than the first cross section; and
a source of pressurized air having a release port mounted to the inlet port of the through passage, whereby airflow from the source of pressurized air through the through passage creates a suction force at the outlet port of the vacuum passage capable of dislodging the object obstructing the person's airway.

12. The device of claim 11, wherein airflow from the source of pressurized air creates a first directional airflow through the through passage and a second directional airflow through the vacuum passage in a direction substantially normal to the first directional airflow.

13. The device of claim 11, wherein a first longitudinal axis extending between the inlet port and the exhaust port of the through passage is substantially aligned with a second longitudinal axis extending between the release port of the source of pressurized air and a base portion of the source of pressurized air opposite the release port.

14. The device of claim 11, wherein the longitudinal axis of the nozzle is substantially aligned with the longitudinal axis of the through passage.

15. The device of claim 11, wherein the constricted portion of the nozzle is characterized by a frustoconical shape.

16. The device of claim 11 further comprising a mouth tube connected to and in communication with the vacuum passage.

17. The device of claim 1 wherein the inlet port includes a passage opening that is oriented at a right angle to a passage opening of the exhaust port.

18. The device of claim 1 wherein the curved passage is downstream the release port and the vacuum passage.

19. The device of claim 1 wherein the through portion is a straight through portion.

* * * * *